(12) United States Patent
Mpock et al.

(10) Patent No.: US 7,235,213 B2
(45) Date of Patent: Jun. 26, 2007

(54) SYSTEM FOR PERFORMING BLOOD COAGULATION ASSAYS AND MEASURING BLOOD CLOTTING TIMES

(75) Inventors: Emmanuel C. Mpock, Salida, CA (US); Ben Clawson, Soquel, CA (US); Sean P. Murphy, Santa Cruz, CA (US)

(73) Assignee: Farallon Medical, Inc., Hayward, CA (US)

( * ) Notice: Subject to any disclaimer, the term of this patent is extended or adjusted under 35 U.S.C. 154(b) by 604 days.

(21) Appl. No.: 10/397,088

(22) Filed: Mar. 25, 2003

(65) Prior Publication Data

US 2003/0180824 A1 Sep. 25, 2003

Related U.S. Application Data

(60) Provisional application No. 60/367,931, filed on Mar. 25, 2002, provisional application No. 60/444,663, filed on Feb. 4, 2003.

(51) Int. Cl.
*G01N 37/00* (2006.01)
*G01N 21/00* (2006.01)
*G01N 1/10* (2006.01)
*G01N 33/00* (2006.01)
*G01N 33/86* (2006.01)
*B01L 3/00* (2006.01)

(52) U.S. Cl. .................. 422/73; 73/64.41; 73/64.43; 356/246; 422/69; 422/102; 436/69

(58) Field of Classification Search .................. 422/69, 422/73, 102; 436/69; 356/246; 73/64.41, 73/64.43

See application file for complete search history.

(56) References Cited

U.S. PATENT DOCUMENTS

| 3,020,748 | A | * | 2/1962 | Marshall et al. ........... 73/64.41 |
| 3,486,859 | A | | 12/1969 | Greiner et al. |
| 3,650,698 | A | | 3/1972 | Adler |
| 3,695,842 | A | | 10/1972 | Mintz |
| 3,836,333 | A | | 9/1974 | Mintz |
| 3,890,098 | A | | 6/1975 | Moreno |
| 3,951,606 | A | | 4/1976 | Moyer et al. |
| 4,034,601 | A | | 7/1977 | Geiger |
| 4,197,734 | A | | 4/1980 | Rosenberg |
| 4,659,550 | A | | 4/1987 | Schildknecht |
| 4,725,554 | A | | 2/1988 | Schildknecht |
| 4,797,369 | A | | 1/1989 | Mintz |
| 4,849,340 | A | | 7/1989 | Oberhardt |
| 4,876,069 | A | | 10/1989 | Jochimsen |
| 5,284,624 | A | | 2/1994 | Behnk |
| 5,302,348 | A | | 4/1994 | Cusack et al. |
| 5,418,141 | A | | 5/1995 | Zweig et al. |
| 5,504,011 | A | | 4/1996 | Gavin et al. |
| 5,580,744 | A | | 12/1996 | Zweig |
| 5,629,209 | A | | 5/1997 | Braun, Sr. et al. |
| 6,002,475 | A | * | 12/1999 | Boyd et al. .................. 356/246 |
| 6,046,051 | A | | 4/2000 | Jina |

* cited by examiner

OTHER PUBLICATIONS

Page 6-8 of Fibrometer Probe Manual, date unknown.

*Primary Examiner*—Jill Warden
*Assistant Examiner*—Lore Ramillano
(74) *Attorney, Agent, or Firm*—Gordon & Rees, LLP

(57) ABSTRACT

A system for performing a blood coagulation assay, having: a reaction chamber; at least one moveable member configured to mix contents of the reaction chamber; a sensor configured to detect the presence of a blood clot formed in the reaction chamber; and a timer that measures an interval of time between when a blood sample is received into the reaction chamber and when the sensor detects the blood clot formed in the reaction chamber.

76 Claims, 5 Drawing Sheets

SYSTEM FOR PERFORMING BLOOD COAGULATION ASSAYS AND MEASURING BLOOD CLOTTING TIMES

This application claims priority under 35 U.S.C. § 119 to U.S. Provisional Application No. 60/367,931 entitled Method and Apparatus for Performing Blood Coagulation Assays and filed on Mar. 25. 2002, and U.S. Provisional Application No. 60/444,663 entitled System for Performing Blood Coagulation Assays and Measuring Blood Clotting Times and filed on Feb. 4. 2003, the entire content of which is hereby incorporated by reference.

TECHNICAL FIELD

The present invention is related in general to systems for performing blood coagulation assays, and in particular to systems for measuring clotting (e.g. prothrombin) times.

BACKGROUND OF THE INVENTION

Coagulation assays have gained acceptance as an important tool for management of patients on anticoagulation therapy for the prevention of clots within their blood vessels. In these assays, a sample of the patient's blood or plasma is tested for coagulation time or "clotting time" which time is related to the patient's dosage of the anticoagulant in the patient's blood. Coagulation assays are also required prior to surgical procedures even for patients not on anticoagulation therapy. This is because the medical professionals need to clearly know the bleeding susceptibility of the patients before they are operated on.

A variety of coagulation tests are presently in use and among the most popular are the "Prothrombin Time" (PT) test and the "Activated Partial Thromboplastin Time" (APTT) test. The PT test is based on the extrinsic coagulation pathway, and the APTT, the intrinsic coagulation pathway. Both pathways result in the formation of a proteolytic enzyme, which catalyzes the formation of the insoluble fibrin fibers from the soluble fibrinogen in the blood.

In nature, the formation of these insoluble fibers results in the formation of a mesh around a cut in the wall of a broken blood vessel, thus preventing excessive bleeding, by trapping and holding back the blood cells. Several zymogens, enzymes and coenzymes are involved in the reactions that lead to the formation of thrombin and subsequently fibrin. The absence of any of these components, which are generally referred to as coagulation factors, can impact the coagulation capability of any blood sample significantly. Each of these factors can be specifically assayed for, to determine deficiency, which is the reason for pre-surgery coagulation tests.

Blood coagulation tests have tended to be complex, and the bulk of them performed generally in centralized clinical laboratories. Clinical or a doctor's office visits on a regular basis to monitor anticoagulation therapy can be very inconvenient and expensive.

Some of the pharmacological agents used in anticoagulation therapy include heparin, protamine and Coumadin, among others. The purity and potency of these agents can vary from batch to batch, making the dosage administration difficult to the medical professional. Patients also respond differently to these agents even for the same dosage. With a very small therapeutic dose window to work with, it is imperative that the effect of these agents be monitored closely and accurately. An excess of each agent could lead to excessive bleeding and the reverse could lead to formation of clots within the blood vessels, with both cases being potentially fatal.

The prior art is replete with various apparatus and methods for measuring the coagulation time of blood samples. Most of them cannot be used for home testing while the others struggle to cope with the challenges posed by the variability exhibited by blood from patient to patient. The following, depict some examples of these devices and methods:

U.S. Pat. No. 3,695,842, which is a 'Method and System for Analyzing a Liquid' issued October 1972 to M.D. Mintz, and assigned to the assignee herein. The patent describes a magnetically coupled mechanical blood clot detection system wherein a variable conductance device is disposed adjacent to a zone containing a liquid and member of ferromagnetic flux lines is formed between the zone and the member. A predetermined variation in the conductance of the device is detected upon change in the magnetic flux lines when the liquid transforms itself and the member is displaced. The signal is produced at the time the predetermined variation in conductance has been detected.

An improved system of the aforementioned method for measuring clotting time is disclosed in U.S. Pat. No. 3,836,333, which is a 'System for Timing the Coagulation of Blood' issued to Michael D. Mintz, on Oct. 30, 1972 and assigned to International Technidyne Corporation, the assignee herein. An electromagnetic coil, which is wound around the reed switch, provides steady-state magnetic flux lines that supplement the flux lines provided by the permanent magnet. When the density of the flux lines passing through the reed switch decreases, as a result of the magnet being displaced, the reed switch opens. The bias coil also provides a magnetic pulse, which forces the reed switch to a closed state. This system is manufactured under the trademark 'HEMOCHRON' by International Technidyne Corporation at Edison, N.J.

U.S. Pat. No. 4,197,734 entitled 'Apparatus for Determining Blood Clotting Time' issued on Apr. 15, 1980 to A. Rosenberg. This patent describes an apparatus, which is capable of measuring the clotting time of blood. The apparatus includes a support frame, which supports a syringe containing a blood sample, and a turntable adapted to rotate at a normal rate of speed. Blood from the syringe drops onto the turntable where the clotting time is automatically and graphically depicted by a chart rotatively carried upon the turntable. The apparatus can also be employed to determine variations in the viscosity of blood plasma and other fluids.

U.S. Pat. No. 3,486,859 entitled 'Blood Analyzing Method and Apparatus' issued on Dec. 30, 1969 to R. Greiner et al. This patent depicts a blood analyzing method and apparatus including a double arm holder having blood liquid reactant chambers, which communicate with each other via a small capillary conduit. An air pump is provided for applying pressure changes to one of the chambers to effect periodic mixing of the liquids via the capillary conduit. An indicator means are included to detect the progressive restriction of the capillary conduit upon coagulation of the blood.

U.S. Pat. No. 4,797,369 entitled 'Method and Apparatus for Detecting a Blood Clot' issued on Jan. 10, 1989 to Michael Mintz, and assigned to the assignee herein. This patent discloses the technique for measuring clot time whereby a sample of whole blood or blood plasma is dispersed into two or more zones. The zones are separated and brought together repeatedly, such that the blood sample is divided into multiple parts, each associated with a zone.

The parts are then rejoined into a single part and the process of separation and joining continues. During the process, a liquid bridge between the separated parties is initially supported by surface tension, but initially collapses at the point of maximum zonal separation. When a fibrin clot is entrained within the rejoining parts, it will align in a direction parallel to the direction of relative motion between the zones. In this manner, a thread appears between the parts as they are being separated. This thread is indicative of a clot, which clot is capable of being detected by visual or electrical means.

U.S. Pat. No. 3,890,098 entitled 'Machine for the Determination of Prothrombin Time and P.T.T.' issued on Jun. 17, 1975 to E. Moreno. This patent describes a reactive material, which is placed in a cup that communicates with a second cup via a restricted orifice. Plasma is placed in the second cup and the reactive material and plasma are moved from cup to cup by a pump until coagulation of the plasma takes place. Means are then provided for stopping the motion of the mixture of reactive material and plasma. Other means are provided for measuring the time required for coagulation.

U.S. Pat. No. 4,725,554 entitled 'Method for Measuring Blood Coagulation Time' issued on Feb. 16, 1988 to K. Schildkenecht. This patent shows a method for measuring the coagulation time of a blood sample, in which a sample reagent mixture is formed by introducing the sample and at least one reagent into a cuvette. The sample reagent mixture is moved in a stationary cuvette so that the mixture flows back and forth around an edge projecting in to the cuvette whereby a clot forms and is detected on this edge. U.S. Pat. No. 4,659,550 entitled 'Method and Apparatus for Measuring Blood Coagulation', describes the same system except that it utilizes photocell detectors to determine the clot formation.

U.S. Pat. No. 5,284,624 entitled 'Method of, and Apparatus for Testing and Measuring Blood Coagulation Time' issued on Feb. 8, 1994 to Holger Behnk. In this method, a liquid reagent and the blood sample are brought together in a cuvette, but separated by a median barrier. The cuvette and its contents are heated to the desired temperature. The cuvette is then pivoted in the measuring station by 90° resulting in a spherical stirring element falling into the reagent, and then into the sample, drawing the latter downward with it, and in that, the measurement is subsequently carried out. The measurement is based on the change in the sample's optical density. The cuvette is fed by a pump, and the spherical stirring element mixing action is driven by a magnetic stirring device. This method is used for an automatic analyzer.

Other methods used, employ multi-layered porous membranes impregnated with reagents, sometimes requiring predetermined blood volumes. The impregnated reagents initiate coagulation producing a detectable signal. Others yet employ the oscillation of magnetic particles suspended in a reagent in a changing electric field. The oscillations change as the blood sample clots. Others yet simply measure the change in light absorbance through a sample before and after the clotting reaction.

Various other systems for measuring blood coagulation and prothrombin times are found in U.S. Pat. Nos. 3,951,606; 4,659,550; and 5,302,348.

Yet another system for measuring prothrombin blood coagulation times is found in the Fibrometer™ system made by Becton, Dickinson and Company of Franklin Lakes, N.J. This system uses a stationary electrode and a moving electrode. Both electrodes are initially placed in the reaction mixture. The moving electrode then cycles up through the reaction mixture in a sweeping elliptical path. The moving electrode has a hooked end that moves in and out of the reaction mixture. When a clot forms in the sample, the clot is lifted out of the reaction mixture. When the clot forms, and is partially lifted out of the reaction mixture by the hooked end of the moving electrode, the clot closes an electrical circuit between the two electrodes such that clot formation is detected by sensing that the circuit between the two electrodes is closed while the moving electrode is in a raised position.

Most of these methods described have severe limitations which make them extremely challenging and near impossible for home use. Some require special blood preparations and handling, making them only suitable for a central clinic with well-trained staff. Some, even though possible for home use, end up being cost-ineffective for the home market. Others require sophisticated equipment with specially trained operators to run them.

The disadvantages of many of these methods, besides cost and the challenge of operation, include the fact that most do not measure coagulation directly. This has been known to pose accuracy problems in many samples. Other methods while appearing to function well, are limited to a narrow range of blood types, therapeutic windows, restricted by a long list of interfering factors and sometimes requiring large volumes of blood.

Methods that employ filtration of the sample as it percolates through its porous membranes are faced with several challenges including wetting and uniform reagent impregnation. Since some of these involve the detection of a signal that is not directly that of fibrin but some other substrate, the accuracy can be seriously compromised while the system is prone to interference from unexpected components in blood, like some medications.

Furthermore, some of these methods have components that are easily contaminated by certain blood components thereby compromising the detectable signal generated, and this could pose a real problem for the home user.

The large blood volume requirements of some of these methods make them impractical for home use. Many of these methods are also limited by what kinds of coagulation tests they can perform due to the reagent chemistry requirements and the detectable signal generated.

SUMMARY OF THE INVENTION

The present invention provides a system for performing a blood coagulation assay. In particular, the present invention provides a system for measuring the time for a blood clot to form after a small amount of blood has been received into a reaction chamber. In preferred aspects, the reaction chamber is coated with a coagulation initiator to cause the clotting process.

Preferably, the walls of the reaction chamber are coated with a blood coagulation initiator such that clot formation commences shortly after the blood enters the reaction chamber. Most preferably, the blood coagulation initiator comprises thromboplastin in a dry form coated on the walls of the reaction chamber. Other suitable blood coagulation initiators include kaolin and diatomaceous earth, which may be especially useful when performing activated prothrombin time test.

When the blood sample enters the reaction chamber, an actuator moves one or more moveable members through the reaction chamber. The moveable member(s) may variously comprise one or more wire prongs or a "paddlewheel" of moveable elements that may extend from a central rotatable element.

In various preferred aspects, the moveable member(s) operate to mix the contents of the reaction chamber (thus speeding and promoting the clotting reaction). In addition, the moveable members may themselves operate to detect the presence of the blood clot, most preferably by simply lifting the blood clot out of the reaction chamber.

The presence of the blood clot (which may preferably be hanging from one of the moveable members) is then sensed by a sensor, and the time in which it takes the blood clot to form is measured by a timer. Most preferably, the time in which it takes for the blood clot to be detected by the device (i.e. after the blood sample has entered/filled the reaction chamber) is then displayed to the operator.

In various preferred aspects, the rotatable members are moved through the blood sample in the reaction chamber such that when a clot forms, the clot becomes entangled on the end of one or more of the moveable member(s) and is lifted out of the reaction chamber.

In various applications, the reaction chamber is simply a curved groove in a block of material and the moveable members comprise a "paddlewheel" design with successive members rotated through the reaction chamber. When a clot eventually forms in the reaction chamber, the clot will be lifted out of the reaction chamber immediately when it becomes entangled on the end(s) of the moveable members.

In preferred aspects, the sensor that detects the presence of the blood clot will comprise an optical sensor that views the clot hanging from the end of one or more of the rotatable members. In preferred aspects, the presence of the clot will be detected by the clot breaking a light path. Alternatively, the presence of the clot can be detected by a change in reflectivity caused by the clot.

Alternatively, the optical sensor may simply view the clot while the clot is still within the reaction chamber. In this aspect, the formation of the clot may disrupt a light path passing through the reaction chamber itself. For example, the reaction chamber may be made of a see-through plastic material with the sensor's beam of light passing through both sides of the reaction chamber.

In still alternate embodiments, the sensor can instead be a weight sensor (that detects the excess force needed to lift the clot out of the reaction chamber—for example, when turning a paddlewheel of moveable members through the reaction chamber). In other alternate embodiments, the sensor can instead be an electrical sensor that signals that the blood clot has completed a circuit between two moveable members (e.g. when the blood clot has been lifted out of the reaction chamber by the moveable members).

An advantage of the present system is its simplicity. Prior art systems for measuring blood coagulation times have relied upon complex chemical reactions to sense the formation of a clot. In contrast, the present invention provides an elegant mechanical solution to the problem. Specifically, when a blood clot forms, it is almost immediately lifted out of the reaction chamber and thus detected. For example, if the "paddle wheel" comprises 8 moveable members and it is rotated once every second, the reaction chamber is "probed" eight times every second to determine exactly when/whether a clot has formed.

As stated above, a further advantage of the present invention is its accuracy. For example, the same moveable members that lift the blood clot out of the reaction chamber are used to stir/mix the contents of the reaction chamber, thereby causing the replication or near replication of the liquid-liquid interface between reagent and blood sample that is found in expensive clinical laboratory systems. Moreover, the moveable members actually quickly pull the blood sample into the reaction chamber, thus giving the reaction a more accurate starting point. This both speeds the reaction along and also ensures that it occurs uniformly in the reaction chamber. Moreover, the present "paddlewheel" design offers the advantage that when a clot forms, it is very quickly detected.

In various preferred aspects, the present invention comprises a separate "base" and a "cartridge". The patient (or other operator) places a drop of blood onto the cartridge, and then inserts the cartridge into the base. The base comprises the sensor and timer functions of the device. The cartridge comprises the reaction chamber and the moveable members that mix the blood (and encounter the blood clot) after the blood sample has been received into the reaction chamber. An actuator (e.g.: a motor) for moving the moveable members is preferably found on the base. Thus, when the cartridge is received into the base of the device, the actuator in the base causes the moveable members in the cartridge to move through the reaction chamber. Since the blood sample is confined to the (disposable) cartridge, a further advantage of the present invention is that the patient never has to clean any blood from the operating elements of the device. As understood herein, "disposable" refers to an item that need only be used a single time, and may then be thrown away. An advantage of the present cartridges being disposable is that it is not necessary to clean blood from them.

A further advantage of the present invention is that it measures clotting time by examining the characteristics of the plasma (e.g.: the fibrin) in the blood, rather than the red blood cells in the blood. In contrast, existing devices examine red blood cells to detect clotting patterns. This has the disadvantage of various individual patient's blood viscosity (i.e. "hematocrit level) being different, thus yielding different results. In contrast, the present invention's reliance on plasma characteristics will yield the same results independent of the patient's blood viscosity. Thus, the present invention can be used either with whole blood samples or with blood plasma.

In an alternate aspect of the present invention, a system of "control" cartridges may also be provided. These control cartridges are provided to periodically test the accuracy of the system, (i.e.: the accuracy of the sensor and timer in the base as well as the "activity" or "validity" of the reagent itself, thus ensuring the reagent has not exceeded its shelf life) as follows. A "test" or "control" cartridge is configured similar to a standard cartridge, except the reaction chamber is coated with a de-calcinated clotting initiator and a control substance expected to yield a specific pre-determined result if the system is working correctly. In preferred aspects, the control substance may include a rationed mixture of coagulation factors and fibrinogen that will form a clot at a predetermined time interval, or any agent that will catalyze the formation of fibrin from fibrinogen. Thus, blood clotting may be simulated simply by adding as drop of calcium chloride solution to the reaction chamber.

Accordingly, whenever an operator wishes to test the accuracy of the device (including testing the strength of the coagulation initiating reagent in the reaction chamber), (s)he simply inserts the control cartridge into the base instead of a regular "blood test" cartridge, and then adds a drop of calcium chloride solution to the "control" cartridge. Then, the operator waits to see the base display the clotting time. This time should be predictable since the chemistry on the reaction chamber (of the control cartridge) is pre-determined. Thus, the operator simply confirms that the simulated blood clot has been detected at the same time that it should have formed. If the systems detects the formation of the simulated blood clot at the same time as the clot was expected to form, the operator is re-assured that the system is operating properly.

It is to be understood that the present invention encompasses both the combination of the base and the cartridge, and the cartridge itself. In both aspects of the invention in which the invention encompasses the cartridge alone, or the cartridge and base together, the cartridge may comprise a reaction chamber, at least one moveable member that moves through the reaction chamber, and a sample receiving chamber in fluid communication with the reaction chamber. The sample receiving chamber is not a critical feature of the invention. For example, the body of the cartridge may be shaped to direct blood flow directly into the reaction chamber without a specific sample reaction chamber being present.

The optional sample receiving chamber may be in fluid communication with the reaction chamber in a variety of ways. For example, a capillary channel may connect the two, or the sample receiving chamber may simply be dimensioned so that the contents of the sample receiving chamber flow into the reaction chamber. In either case, an additional advantage of the paddlewheel is that it may pull blood quickly into the reaction chamber.

The sample receiving chamber is the location in which the patient drops a drop of blood to be tested. A portion of this drop of blood will then flow into the reaction chamber to be tested. An advantage of the present system is that the reaction chamber can be very small (which makes the present system very accurate as a more uniform reaction occurs, and time is not wasted "searching" for a clot in a large reaction chamber). Most preferably, the reaction chamber has a volume of about 5 ul to 40 ul, and more preferably 10 ul to 25 ul, and most preferably 10 ul to 15 ul. An advantage of not requiring more than 25 ul of blood is that 25 ul is roughly equivalent to a "hanging drop" of blood. As such, a single drop of blood is sufficient for operation of the present invention. In optional aspects, an overflow channel may be connected to the reaction chamber to limit the maximum mount of blood in the reaction chamber.

A single cover may be provided over both the reaction chamber and the moveable members passing therethrough. In addition, a retaining wall may be positioned adjacent to either the sample receiving chamber, or the reaction chamber, or both. The retaining wall may preferably be dimensioned such that when a finger is positioned against the retaining wall, the finger is positioned over the sample receiving well, such that it operates as a "finger guide", as follows. The patient simply pricks their finger to obtain a drop of blood and then places their finger (or the patient's finger when an operator is assisting a patient) against the retaining wall. The retaining wall is preferably dimensioned such that when the finger rests against it, the blood will drop directly into the sample receiving chamber positioned therebelow. An advantage of such a finger guide is that it makes the present invention especially easy for elderly patients (or any patient with shaky hands) to use.

A particular advantage of using a dry coating (as opposed to a fluid reagent) is that it extends the shelf life of the cartridges. A second advantage of using a dry coating of coagulation initiator on the inner walls of the reaction chamber is that the operator need not mix, pour or otherwise deal with liquid reactants. In contrast, some existing systems require an operator to mix and prepare various solutions during system operation.

In optional aspects of the invention, additional optical systems may be used to detect the fluid level in the reaction chamber such that the timer is started only when a sufficient level of blood is present in the reaction chamber.

An additional advantage of the moveable members of the present invention is that they may actually pull blood into the reaction chamber, thus quickly mixing the blood with the coagulation initiator. This has the effect of giving the reaction a more accurate starting point. In addition, the mixing by the moveable members accelerates the uniform dissolution and distribution of the reagent within the reaction chamber. Moreover, such mixing also ensures uniform distribution of heat within the reaction chamber during the reaction.

A further advantage of the present invention is that it can be used to perform coagulation assays that do not require separation of the plasma sample from the whole blood, but instead can be performed on both, as circumstances require.

Further advantages include the present invention's ability to perform assays on very small blood samples and the fact that no preparation of a reagent-containing solution is required.

Although the present invention preferably uses thromboplastin as the coagulation initiating reagent in its reaction chamber, it is not so limited. Rather, the present invention is advantageously adapted to accommodate all types of reagents used for coagulation, regardless of whether they are custom formulated or off the shelf.

As can be seen, the present invention provides a very simple system in which an operator need only insert a single drop of blood, and then read out their results. Thus, the present invention can easily be used at home.

DETAILED DESCRIPTION OF THE DRAWINGS

Figure 1:
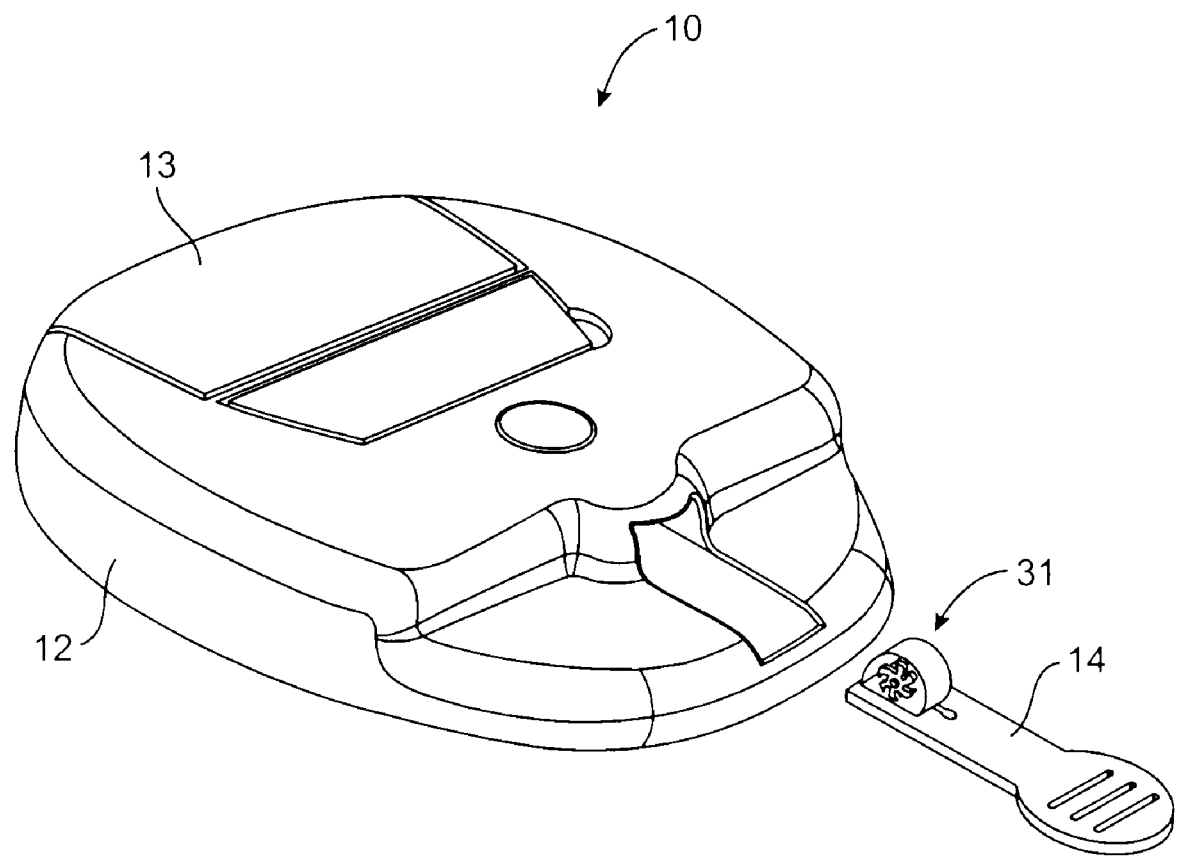
FIG. 1 is a perspective view of the cartridge and base of the present invention.
Figure 2:
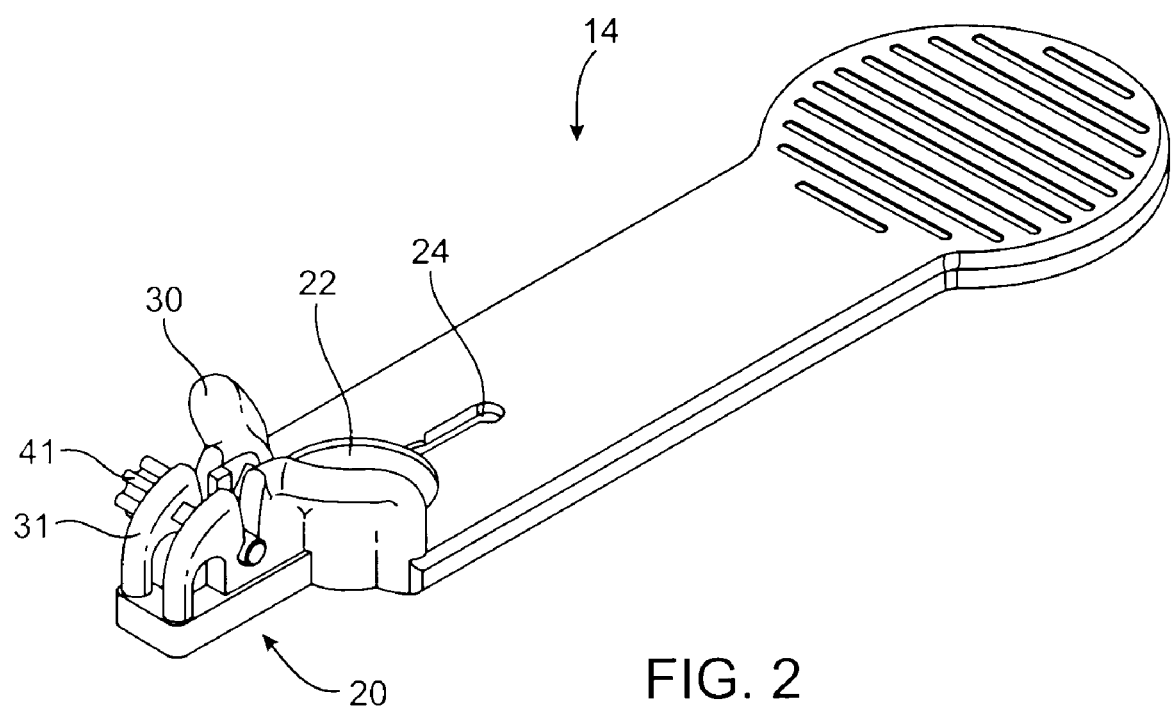
FIG. 2 is a perspective view of the cartridge of the present invention.

In preferred aspects, the present invention provides a system for performing a blood coagulation assay, including: a reaction chamber with a dry coagulation initiator therein; at least one moveable member configured to move through the reaction chamber and mix contents of the reaction chamber; a sensor configured to detect the presence of a blood clot formed in the reaction chamber; and a timer that measures an interval of time between when a blood sample is received into the reaction chamber and when the sensor detects the blood clot formed in the reaction chamber.

In preferred aspects, the present invention also provides a system for performing a blood coagulation assay, including: a reaction chamber; at least one moveable member configured to mix contents of the reaction chamber; a sensor configured to detect the presence of a blood clot formed in the reaction chamber; and a timer that measures an interval of time between when a blood sample is received into the reaction chamber and when the sensor detects the blood clot formed in the reaction chamber.

In preferred aspects, the present invention also provides a system for performing a blood coagulation assay, comprising: a cartridge including: a reaction chamber, and at least one moveable member configured to move through the reaction chamber and mix contents of the reaction chamber; and a base including: a sensor configured to detect the presence of a blood clot formed in the reaction chamber; and a timer that measures an interval of time between when a blood sample is received into the reaction chamber and when the sensor detects the blood clot formed in the reaction chamber; wherein the cartridge is receivable into the base unit.

In preferred aspects, the present invention also provides a method of performing a blood coagulation assay, including: placing a drop of whole blood or blood plasma into a reaction chamber (preferably having a dry coagulation initiator disposed therein); mixing the contents of the reaction chamber with a moveable member passing through the reaction chamber, thereby coagulating the blood in the reaction chamber so as to form a blood clot; detecting the presence of the blood clot; and determining an interval of time between when a blood sample is received into the reaction chamber and when the sensor detects the formation of the blood clot in the reaction chamber.

In preferred aspects, the present invention also provides a method of testing a system for performing a blood coagulation assay, including: placing a drop of calcium chloride solution into a reaction chamber (preferably having a dry de-calcinated coagulation initiator and a control substance disposed therein); mixing the contents of the reaction chamber with a moveable member passing through the reaction chamber, thereby forming a clot in the reaction chamber; detecting the presence of the clot; and determining an interval of time between when the calcium chloride solution is received into the reaction chamber and when the sensor detects the formation of the clot in the reaction chamber.

Referring first to FIG. 1, the present invention provides a system 10 for performing a blood coagulation assays. In preferred embodiments, system 10 includes a base 12 and a disposable cartridge 14. As will be more fully explained herein, a patient simply inserts cartridge 14 into base 12 and then places a drop of blood onto cartridge 14. Sensor and timing functions within base 12 then determine the clotting time of the blood sample, with an optional LED indicator 13 on base 12 displaying the clotting time. Cartridges 14 are disposable single-use devices. Moreover, cartridges 14 fully enclose the drop of blood received therein. Thus, there is no physical contact between the blood sample and base 12, and thus no need for an operator/patient to wipe or clean blood from the device between uses.

Cartridge 14 may be made of plastic or any suitable material which preferably has good thermal conductivity, clarity for optical transmission, mechanical properties for easy molding, surface properties that allow for uniform coating and stability of reagent, and neutrality to the liquid medium to prevent interference with the assay. For this purpose, suitable plastics include those with high free surface energies and low water sorption, including PETG, polyester (Mylar®), polycarbonate (Lexan®), polyvinyl chloride, polystyrene, SAN, acrylonitrile-butadiene-styrene (ABS), particularly ABS supplied by Borg Warner under the trade name Cycolac, among others. These plastic materials described are all hydrophobic and would make it difficult to coat the reaction chamber and channel with reagents. The molded parts can therefore simply be plasma etched or corona treated to render them hydrophilic.

FIGS. 2, 3, 4 and 5 further illustrate preferred details of cartridge 14, as follows. Cartridge 14 includes a reaction chamber 20, a sample receiving chamber 22 and an overflow chamber 24 formed into the body of cartridge 14, as shown.

Reaction chamber 20 is preferably deeper than sample receiving chamber 22. In addition, overflow chamber 24 is preferably deeper than sample receiving chamber 22. Cartridge 14 also preferably includes a retaining wall 30. Retaining wall 30 is preferably dimensioned such that when an operator/patient places a finger F there against, a drop of blood B from finger F will fall directly downward into sample receiving chamber 22. In optional embodiments wherein a sample receiving chamber 22 is not present, cartridge 14 may be dimensioned such that blood flows directly into reaction chamber 20 when finger F is placed against retaining wall 30. Blood in sample receiving chamber 22 will move into reaction chamber 20 (due to the increased depth of reaction chamber 20, or due to the bottom of sample receiving chamber 22 being sloped downwardly towards reaction chamber 20, or both). When reaction chamber 20 fills to a desired level, any excess blood will flow back through sample receiving chamber 22 and into overflow chamber 24. Thus, the presence of overflow chamber 24 ensures that the liquid level in reaction chamber 20 is at a desired level.

In preferred aspects, reaction chamber 20 has a coagulation initiator therein. Preferably, the coagulation initiator is a thromboplastin, but need not be so. For example, kaolin or diatomaceous earth may also be used. Most preferably, the coagulation initiator is a dried reagent that is most preferably coated on the interior of reaction chamber 20.

Preferred modes for applying such a coagulation initiating reagent to the reaction chamber 20 include spraying, painting, lyophilization, evaporation, adsorption, covalent conjugation or the like. For reagents with large particulate components, spray painting or lyophilization would be adequate. Biodeposition results in instantaneous drying when dispensed at room temperature due to the size of the drops. A typical Prothrombin Time coagulation assay would typically use a total of 0.5 mL of a recombinant tissue factor reagent of a concentration of 10 micrograms per milliliter for a 20 mL sample of blood.

Figure 3:
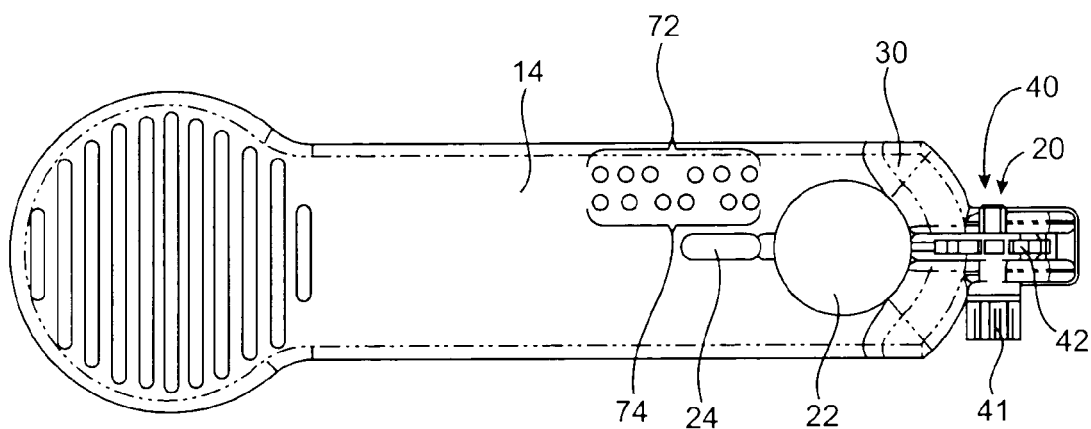
FIG. 3 is a top plan view of the cartridge of the present invention.
Figure 4:
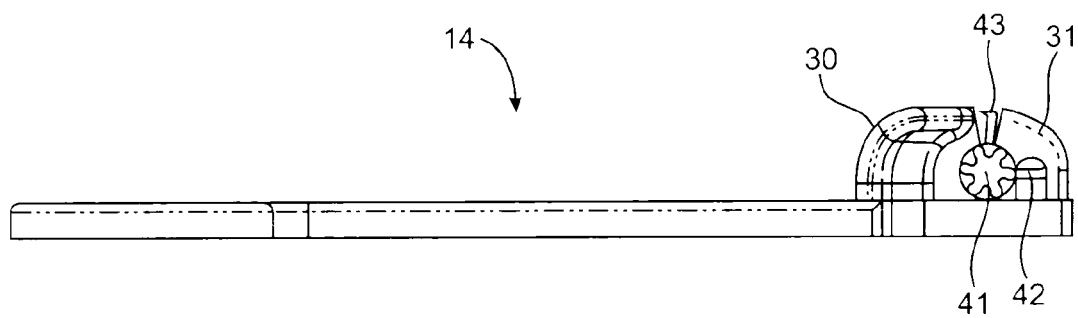
FIG. 4 is a side elevation view of the cartridge of the present invention.
Figure 5:
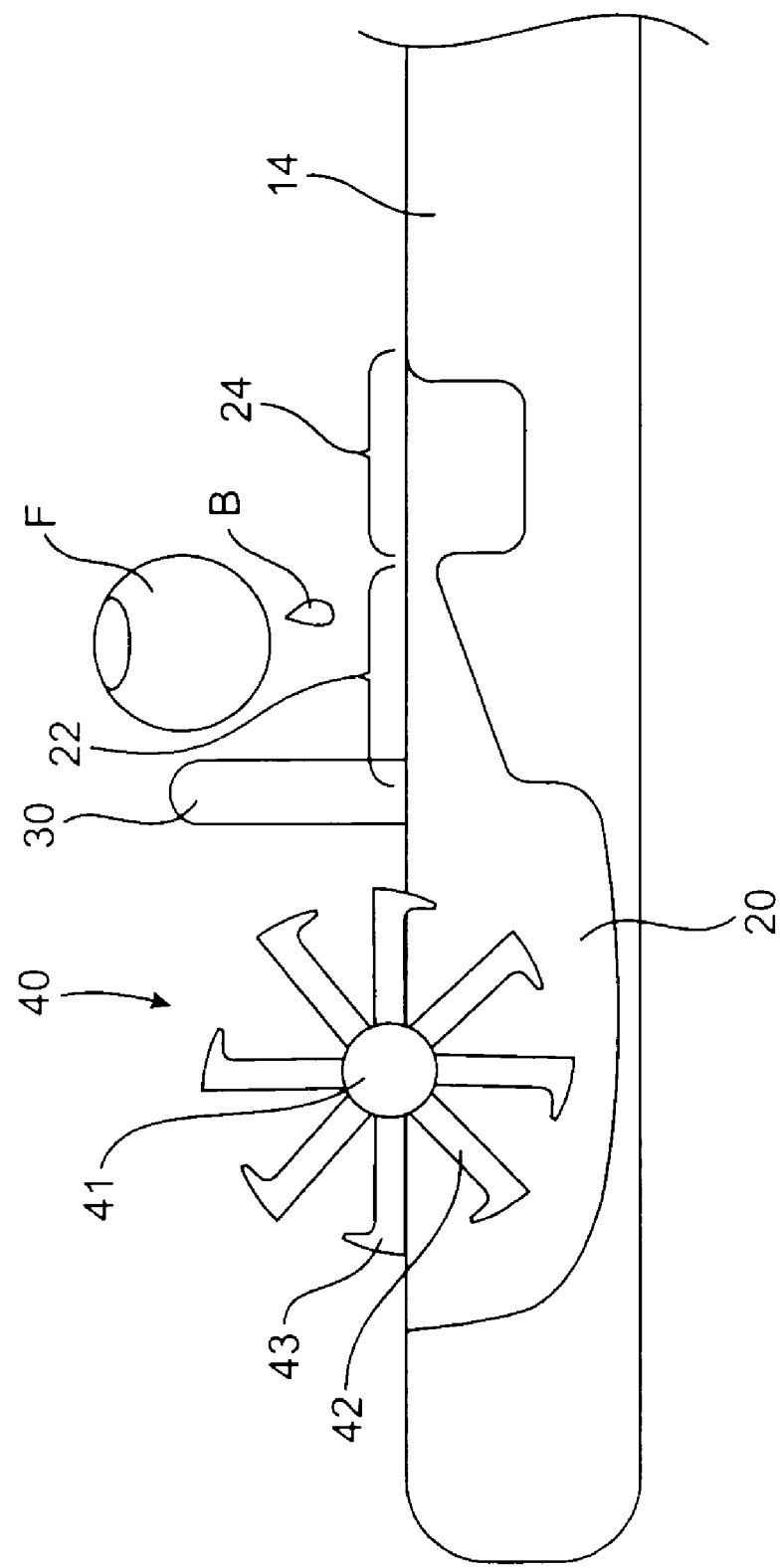
FIG. 5 is a sectional side elevation view of the end of the cartridge that is inserted into the base.

As is also shown in FIGS. 3, 4 and 5, a "paddlewheel" 40 of moveable members 42 are provided, with moveable members 42 positioned such that when they are rotated about a central rotatable element 41, moveable members 42 stir/mix the contents of reaction chamber 20. Optionally, moveable members 42 may each have hooked or pointed or curved ends 43. When cartridge 14 is received into base 12, an actuator (not shown) in base 12 will cause central rotatable element 41 to rotate, thus sequentially rotating moveable members 42 through reaction chamber 20.

In accordance with the present invention, a blood clot will form within reaction chamber 20. Very quickly after it forms, such blood clot will be lifted out of reaction chamber 20 when it becomes entangled on one or more of moveable members 42.

As will be explained, a sensor in base 12 is configured to detect the presence of the blood clot, and a timer in base 12 measures the interval of time between when the blood sample is received into reaction chamber 20 and when the blood clot forms.

Returning to the moveable members 42 shown in FIGS. 3 to 5, it is to be understood that the present invention is not so limited. For example, only one moveable member 42 may be used. However, using greater numbers of moveable members 42 has the advantage that a blood clot is lifted from the reaction chamber 20 sooner. (Increasing the speed at which paddlewheel 40 is rotated would have the same effect). Alternative designs are possible. For example, the at least one moveable member 42 may instead comprise one or more wire prongs. Also, the moveable member(s) 42 may rotate one way in a circular path through the reaction chamber 20, or they may be moved back and forth in an arcuate path (similar to the movement of a pendulum). Additionally, the moveable members 42 may all be disposed for movement in the same plane (as shown in FIG. 5) or they may be disposed for movement in parallel planes. Additionally, the hooked/curved/pointed ends 43 of moveable members 42 are not limiting. Various designs are possible, all keeping within the scope of the present invention.

To advantageously affect stirring/mixing of blood and coagulation initiating reagent in reaction chamber 20, reaction chamber 20 preferably has a curved bottom without any sharp corners. In preferred aspects, the width of reaction chamber 20 is preferably less than 3.5 mm. In preferred aspects, the volume of reaction chamber 20 is preferably between 5 ul and 40 ul.

In preferred aspects, the volume of sample receiving chamber 22 is less than 20 ul (i.e.: less than the volume of a typical "hanging drop" of blood).

In optional preferred aspects, a cover 31 is positioned over reaction chamber 20 and moveable member(s) 42.

Figure 6:
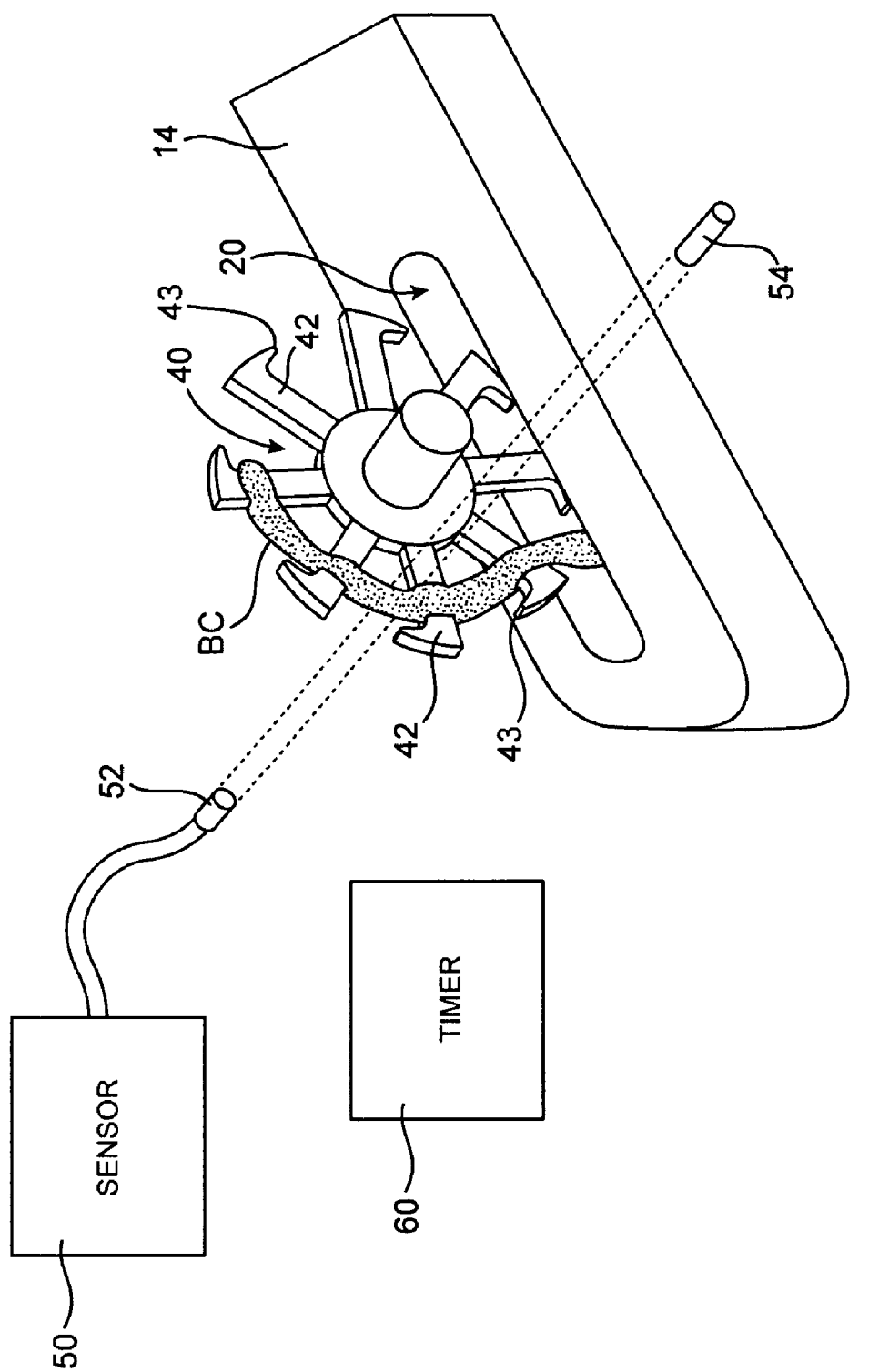
FIG. 6 schematically illustrates the operation of the sensor and timer functions of the present invention.

As stated above, the present invention comprises a sensor 50 and a timer 60, both of which are preferably disposed in base 12. The operation of the sensor and timer functions are schematically illustrated in FIG. 6, as follows. Cartridge 14 having reaction chamber 20 is provided. As paddlewheel 40 is rotated, moveable members 42 stir the contents of reaction chamber 20. A blood clot BC then forms within reaction chamber 20 and is lifted out of reaction chamber 20 by moveable members 42. In accordance with one aspect of the invention, sensor 50 includes an eye 52 that is positioned to receive light from a light source 54. A timer 60 is also provided. Preferably, sensor 50, eye 52, light source 54 and timer 60 are all disposed within base 12.

In accordance with one preferred aspect of the present invention, eye 52 and sensor 50 detects the presence of blood clot BC by detecting a change in the light passing between light source 54 and eye 52. Such change may comprise a change in reflectivity caused by the presence of blood clot BC. Such change may also simply comprise a break in the light path for a greater than expected period of time, as follows. As paddlewheel 40 rotates, each of moveable members 42 will sequentially break the light path passing between light source 54 and eye 52. Knowing the speed of rotation of paddlewheel 40 and the width and number of each of moveable members 42, the presence of blood clot BC can be detected simply by viewing an apparent "increase" in the width of a moveable member 42 (since the blood clot will be hanging on the member). In optional preferred aspects, an apparent increase in the view width of a moveable member 42 of at least 15% would be sufficient to trigger a positive blood clot result.

In accordance with another preferred aspect of the present invention, eye 52 and light source 54 are positioned such that the light beam passes instead directly through the body of cartridge 14 and through reaction chamber 20. In this aspect, at least a portion of cartridge 14 is made of a clear light transmitting material. In this aspect of the invention, sensor 50 would be able to detect blood clot BC while blood clot BC is still in reaction chamber 20.

In alternate aspects of the invention, two different moveable members 42 may be connected to electrodes. Sensor 50 may then include an electrical sensor that detects a circuit being completed by a blood clot that is held between two moveable members 42 when the moveable members 42 both have lifted the blood clot out of the reaction chamber 20.

In optional preferred aspects of the invention, the coagulation initiator is de-calcified and a control substance is also provided in reaction chamber 20. In this aspect of the invention, simply adding a drop of calcium chloride solution to the reaction chamber 20 will simulate blood clotting. This aspect of the invention is especially useful when testing the accuracy of the present invention. Moreover, this aspect of the invention tests both the potency of the reagent and the mechanics of the device. Thus, the entire overall system is checked. Specifically, by simulating blood clotting with a control substance and a de-calcified coagulation initiator, it is possible to test the accuracy of the device assuming the strength of the coagulation initiator is known).

Thus, in accordance with optional preferred aspects of the present invention, a cartridge 14 having both a control substance and a coagulation initiator in its reaction chamber 20 is also provided with indicia 72 and 74 (FIG. 3) indicating the strength of the strength of the dry coagulation initiator. In optional preferred aspects, as shown in FIG. 3, the indicia comprise two series of parallel raised portions 72 and 74 on cartridge 14. In this optional aspect of the invention, the relative locations of the parallel series of raised portions 72 and 74 is indicative of the strength/potency of the reagent used. It is to be understood that the present invention is not limited to series of raised portions 72 and 74 indicating reagent strength. Any suitable machine readable format (e.g.: collinear dots thereon) may instead be used. As cartridge 14 is inserted into base 12, an optical reader compares the positions of raised portions 72 and 74, thus determining the strength of the coagulation initiator. In preferred aspects, raised portions 72 and 74 are "bumps" that are arranged so that they represent binary digits. Specifically, the presence or absence of the bumps at expected locations along the body of cartridge 14 can be indicative of a "1" or a "0" in binary format. Additionally, a separate optical detector can be used to read each series of bumps. An advantage of using two series of raised portion indicators is that cartridge 14 can be inserted into base 12 at different speeds (by different patients) without compromising the easy machine readable format of the indicia.

It is to be understood that the present invention comprises both the disposable cartridges 14 and also the working combination of disposable cartridges 14 as received into, and operated with, base 12.

Other optional aspects of the invention include a sensor configured to detect the liquid level in reaction chamber 20.

In further optional aspects base 12 may include a heater. Such heater would be especially useful for temperature sensitive assays like timed coagulation tests such as Prothrombin Time determination, with the temperature held constant through the duration of the assay.

The present invention also provides novel methods, as follows. First, the present invention provides a method of performing a blood coagulation assay, including: placing a drop of whole blood or blood plasma into sample receiving chamber 22; moving a portion of the blood from the sample receiving chamber 22 into reaction chamber 20 having a dry coagulation initiator disposed therein; mixing the contents of the reaction chamber 20 with moveable member(s) 42 passing through the reaction chamber 20, thereby coagulating the blood in reaction chamber 20 so as to form a blood clot BC; detecting the presence of blood clot BC; and determining an interval of time between when a blood sample is received into the reaction chamber 20 and when the sensor 50 detects the formation of the blood clot in the reaction chamber 20.

In various aspects, moving a portion of the blood from sample receiving chamber 22 into reaction chamber 20 includes pulling a portion of the blood into the reaction chamber 20 with the moveable member 42.

In various aspects, placing a drop of whole blood or blood plasma into sample receiving chamber 22 includes positioning the end of a patient's finger against a retaining wall 30 adjacent to the sample receiving chamber 22, thereby positioning the end of the finger over sample receiving chamber 22.

Secondly, the present invention provides a method of testing a system for performing a blood coagulation assay, by placing a drop of calcium chloride solution into sample receiving chamber 22; moving a portion of the calcium chloride solution from sample receiving chamber 22 into reaction chamber 20 having a dry de-calcinated coagulation initiator and a control substance disposed therein; mixing the contents of reaction chamber 20 with a moveable member 42 passing through reaction chamber 20, thereby forming a clot in reaction chamber 20; detecting the presence of the clot; and determining an interval of time between when the calcium chloride solution is received into the reaction chamber 20 and when sensor 50 detects the formation of the clot in the reaction chamber 20.

What is claimed is:

1. A system for performing a blood coagulation assay, comprising: a reaction chamber with a dry coagulation initiator therein; at least one moveable member configured to move through the reaction chamber and mix contents of the reaction chamber; a sensor configured to detect the presence of a blood clot formed in the reaction chamber; and a timer that measures an interval of time between when a blood sample is received into the reaction chamber and when the sensor detects the blood clot formed in the reaction chamber, wherein the at least one moveable member lifts the blood clot out of the reaction chamber, and wherein the at least one moveable member comprises a plurality of members extending radially from a central rotatable member.

2. The system of claim 1, wherein the dry coagulation initiator comprises a material selected from the group consisting of thromboplastin, kaolin or diatomaceous earth.

3. The system of claim 1, wherein the dry coagulation initiator is coated on the interior of the reaction chamber.

4. The system of claim 1, wherein the reaction chamber is shaped as an arched groove, such that the distal ends of each of the moveable members sequentially pass through the reaction chamber as the central rotatable member is rotated.

5. The system of claim 4, wherein the width of the reaction chamber is less than 3.5 mm.

6. The system of claim 1, wherein the reaction chamber has a curved bottom without any sharp corners.

7. The system of claim 1, wherein the reaction chamber has a volume of between 5 ul and 40 ul.

8. The system of claim 1, further comprising: a sample receiving chamber in fluid communication with the reaction chamber.

9. The system of claim 8, wherein the sample receiving chamber has a volume of less than 20 ul.

10. The system of claim 8, further comprising: a cover over the reaction chamber and the at least one moveable member.

11. The system of claim 8, further comprising: a retaining wall positioned adjacent to the sample receiving chamber, wherein the retaining wall is dimensioned such that when an operator places the end of the finger against the retaining wall, the finger is positioned over the sample receiving chamber.

12. The system of claim 1, wherein the sensor detects the blood clot while the blood clot is in the reaction chamber.

13. The system of claim 1, wherein the sensor detects the blood clot when the at least one moveable member encounters a blood clot in the reaction chamber.

14. The system of claim 1, wherein the sensor is an optical sensor that views the contents of the reaction chamber along an optical path that passes through the reaction chamber.

15. The system of claim 1, wherein the sensor is an optical sensor, further comprising: a light source, wherein the light source is positioned on one side of the moveable member and the optical sensor is positioned on the other side of the moveable member, and wherein the optical sensor detects a change in a light path from the light source to the optical sensor caused by a blood clot hanging from the at least one moveable member.

16. The system of claim 15, wherein the change is viewed as an apparent increase in the width of the at least one moveable member and as a decrease in spacing between successive moveable members due to the presence of a blood clot on the at least one moveable member.

17. The system of claim 1, wherein the sensor is an optical sensor that detects a change in reflectivity caused by the presence of a blood clot.

18. The system of claim 1, wherein the sensor is an electrical sensor that detects a circuit being completed by current passing through a blood clot held between two moveable members.

19. The system of claim 1, wherein the coagulation initiator is de-calcified, and wherein the reaction chamber comprises an agent that catalyzes fibrin formation from fibrinogen therein such that blood clotting is simulated by adding a drop of calcium chloride solution to the reaction chamber.

20. The system of claim 1, wherein the reaction chamber and the at least one moveable member are disposed on a cartridge and the sensor and the timer are disposed in a base, and wherein the cartridge is receivable into the base.

21. A system for performing a blood coagulation assay, comprising: a reaction chamber; at least one moveable member configured to mix contents of the reaction chamber; a sensor configured to detect the presence of a blood clot formed in the reaction chamber; and a timer that measures an interval of time between when a blood sample is received into the reaction chamber and when the sensor detects the blood clot formed in the reaction chamber, wherein the at least one moveable member lifts the blood clot out of the reaction chamber, and wherein the at least one moveable member comprises a plurality of members extending radially from a central rotatable member.

22. The system of claim 21, wherein the reaction chamber has a volume of between 5 ul and 40 ul.

23. The system of claim 21, further comprising: a sample receiving chamber in fluid communication with the reaction chamber.

24. The system of claim 21, further comprising: a retaining wall positioned adjacent to the sample receiving chamber, wherein the retaining wall is dimensioned such that when an operator places the end of the finger against the retaining wall, the finger is positioned over the sample receiving chamber.

25. The system of claim 21, wherein the sensor detects the blood clot while the blood clot is in the reaction chamber.

26. The system of claim 21, further comprising: a dry coagulation initiator in the reaction chamber.

27. The system of claim 26, wherein the coagulation initiator is de-calcified, and wherein the reaction chamber comprises an agent that catalyzes fibrin formation from fibrinogen therein such that blood clotting is simulated by adding a drop of calcium chloride solution to the reaction chamber.

28. The system of claim 21, wherein the reaction chamber and the at least one moveable member are disposed on a cartridge and the sensor and the timer are disposed in a base, and wherein the cartridge is receivable into the base.

29. The system of claim 28, further comprising: machine readable marks indicating the strength of the dry coagulation initiator, the machine readable marks being disposed on the cartridge.

30. The system of claim 29, wherein the machine readable marks comprise a series of raised portions on the cartridge.

31. The system of claim 29, wherein the machine readable marks are printed on the cartridge.

32. A system for performing a blood coagulation assay, comprising: a cartridge comprising: a reaction chamber, and at least one moveable member configured to move through the reaction chamber and mix contents of the reaction chamber; and a base comprising: a sensor configured to detect the presence of a blood clot formed in the reaction chamber; and a timer that measures an interval of time between when a blood sample is received into the reaction chamber and when the sensor detects the blood clot formed in the reaction chamber; wherein the cartridge is receivable into the base, wherein the at least one moveable member lifts the blood clot out of the reaction chamber, and wherein the at least one moveable member comprises a plurality of members extending radially from a central rotatable member.

33. The system of claim 32, further comprising: a dry coagulation initiator in the reaction chamber.

34. The system of claim 33, wherein the coagulation initiator is decalcified, and wherein the reaction chamber comprises a control substance therein such that blood clotting is simulated by adding a drop of calcium chloride solution to the reaction chamber.

35. The system of claim 33, further comprising: machine readable marks indicating the strength of the dry coagulation initiator, the machine readable marks being disposed on the cartridge.

36. The system of claim 35, wherein the machine readable marks comprise a series of raised portions on the cartridge.

37. The system of claim 35, wherein the machine readable marks are printed on the cartridge.

38. The system of claim 32, wherein the at least one moveable member rotates through the reaction chamber.

39. The system of claim 38, wherein the at least one moveable member rotates one way in a circular path.

40. The system of claim 38, wherein the at least one moveable member rotates back and forth in an arcuate path.

41. The system of claim 32, wherein the at least one moveable member comprises one or more wire prongs.

42. The system of claim 32, wherein the plurality of members move in the same plane.

43. The system of claim 32, wherein the plurality of members move in parallel planes.

44. The system of claim 32, wherein the moveable members have curved ends.

45. The system of claim 32, wherein the moveable members have hooked or pointed ends.

46. The system of claim 45, wherein the hooked or pointed ends extend in a direction generally perpendicular to the member.

47. The system of claim 32, wherein the reaction chamber is shaped as an arched groove, such that the distal ends of each of the moveable members sequentially pass through the reaction chamber as the central rotatable member is rotated.

48. The system of claim 47, wherein the width of the reaction chamber is less than 3.5 mm.

49. The system of claim 32, wherein the reaction chamber has a curved bottom without any sharp corners.

50. The system of claim 32, wherein the reaction chamber has a volume of between 5 ul and 40 ul.

51. The system of claim 32, further comprising: a sample receiving chamber in fluid communication with the reaction chamber.

52. The system of claim 51, wherein the sample receiving chamber has a volume of less than 20 ul.

53. The system of claim 51, further comprising: a retaining wall positioned adjacent to the sample receiving chamber, wherein the retaining wall is dimensioned such that when an operator places the end of the finger against the retaining wall, the finger is positioned over the sample receiving chamber.

54. The system of claim 32, further comprising: an overflow chamber in fluid communication with the reaction chamber, the overflow chamber positioned to limit maximum fluid level within the reaction chamber.

55. The system of claim 32, wherein the sensor detects the blood clot while the blood clot is in the reaction chamber.

56. The system of claim 32, wherein sensor detects the blood clot when at least one moveable member has lifted the blood clot out of the reaction chamber.

57. The system of claim 32, wherein the sensor is an optical sensor that views the contents of the reaction chamber along an optical path that passes through the reaction chamber.

58. The system of claim 32, wherein the sensor is an optical sensor, further comprising: a light source, wherein the light source is positioned on one side of the moveable member and the optical sensor is positioned on the other side of the moveable member, and wherein the optical sensor detects a change in a light path from the light source to the optical sensor caused by a blood clot hanging from the at least one moveable member.

59. The system of claim 58, wherein the change is viewed as an apparent increase in the width of the at least one moveable member and as a decrease in spacing between successive moveable members due to the presence of a blood clot on the at least one moveable member.

60. The system of claim 32, wherein the sensor is an optical sensor that detects a change in reflectivity caused by the presence of a blood clot.

61. The system of claim 32, wherein the sensor is an electrical sensor that detects a circuit being completed by current passing through a blood clot held between two moveable members.

62. The system of claim 32, further comprising: a sensor configured to detect a fluid level in the reaction chamber.

63. A cartridge for insertion into a system for performing a blood coagulation assay, comprising: a reaction chamber; and at least one moveable member configured to move through the reaction chamber and mix contents of the reaction chamber, wherein the at least one moveable member lifts clotted material out of the reaction chamber, and wherein the at least one moveable member comprises a plurality of members extending radially from a central rotatable member.

64. The cartridge of claim 63, wherein the cartridge is disposable.

65. The cartridge of claim 63, further comprising: a dry coagulation initiator in the reaction chamber.

66. The system of claim 63, wherein the dry coagulation initiator comprises a material selected from the group consisting of thromboplastin, kaolin or diatomaceous earth.

67. The system of claim 63, wherein the dry coagulation initiator is coated on the interior of the reaction chamber.

68. The system of claim 63, wherein the at least one moveable member rotates through the reaction chamber.

69. The system of claim 63, wherein the reaction chamber is shaped as an arched groove, such that the distal ends of each of the moveable members sequentially pass through the reaction chamber as the central rotatable member is rotated.

70. The system of claim 63, wherein the reaction chamber has a volume of between 5 ul and 40 ul.

71. The system of claim 63, further comprising: a sample receiving chamber in fluid communication with the reaction chamber.

72. The system of claim 71, wherein the sample receiving chamber has a volume of less than 20 ul.

73. The system of claim 71, further comprising: a retaining wall positioned adjacent to the sample receiving chamber, wherein the retaining wall is dimensioned such that when an operator places the end of the finger against the retaining wall, the finger is positioned over the sample receiving chamber.

74. The system of claim 63, wherein the reaction chamber has a curved bottom without any sharp corners.

75. The system of claim 69, further comprising: a cover over the reaction chamber and the at least one moveable member.

76. A cartridge for insertion into a system for performing a blood coagulation assay, comprising: a reaction chamber; and at least one moveable member configured to move through the reaction chamber and mix contents of the reaction chamber, wherein the reaction chamber has a volume of between 5 ul and 40 ul, and wherein the at least one moveable member comprises a plurality of members extending radially from a central rotatable member.

* * * * *